United States Patent [19]
Carleton et al.

[11] 3,960,449
[45] June 1, 1976

[54] MEASUREMENT OF ANGULAR DEPENDENCE OF SCATTERED LIGHT IN A FLOWING STREAM

[75] Inventors: Joseph G. Carleton; Richard G. Sweet, both of Palo Alto, Calif.

[73] Assignee: The Board of Trustees of Leland Stanford Junion University, Stanford, Conn.

[22] Filed: June 5, 1975

[21] Appl. No.: 583,883

[52] U.S. Cl. .............................. 356/103; 250/574
[51] Int. Cl.² ........................................ G01N 21/00
[58] Field of Search .......... 356/102, 103, 104, 208, 356/181; 250/574; 356/39

[56] References Cited
UNITED STATES PATENTS

| | | | |
|---|---|---|---|
| 3,422,667 | 1/1969 | Hrdina | 356/181 |
| 3,713,743 | 1/1973 | Simms | 356/104 |
| 3,822,095 | 7/1974 | Hirschfeld | 356/39 |
| 3,835,315 | 9/1974 | Gravitt, Jr. | 356/103 |
| 3,869,209 | 3/1975 | Sigrist | 356/103 |

*Primary Examiner*—John K. Corbin
*Assistant Examiner*—Conrad Clark
*Attorney, Agent, or Firm*—Donovan J. De Witt

[57] ABSTRACT

Particle analyzing method and apparatus are provided for measuring the intensity of light scattered from a particle as a function of angle. Particles such as biological cells are contained in a stream for travel along a path which includes a scatter line along which the particles pass successively. A beam of collimated monochromatic radiation is directed onto the flow path, and detector means are provided having a radiation acceptance geometry whose projection intercepts the beam along the scatter line. The projected acceptance geometry includes an aperture image located adjacent the scatter line and having a dimension in the direction of travel of the particles which is substantially less than the length of the scatter line such that the angle of scatter radiation detectable by the detector means varies according to the position of the particle along the scatter line. The output from the detector provides a measure of the scatter light intensity versus angle characteristic of the particle.

22 Claims, 7 Drawing Figures

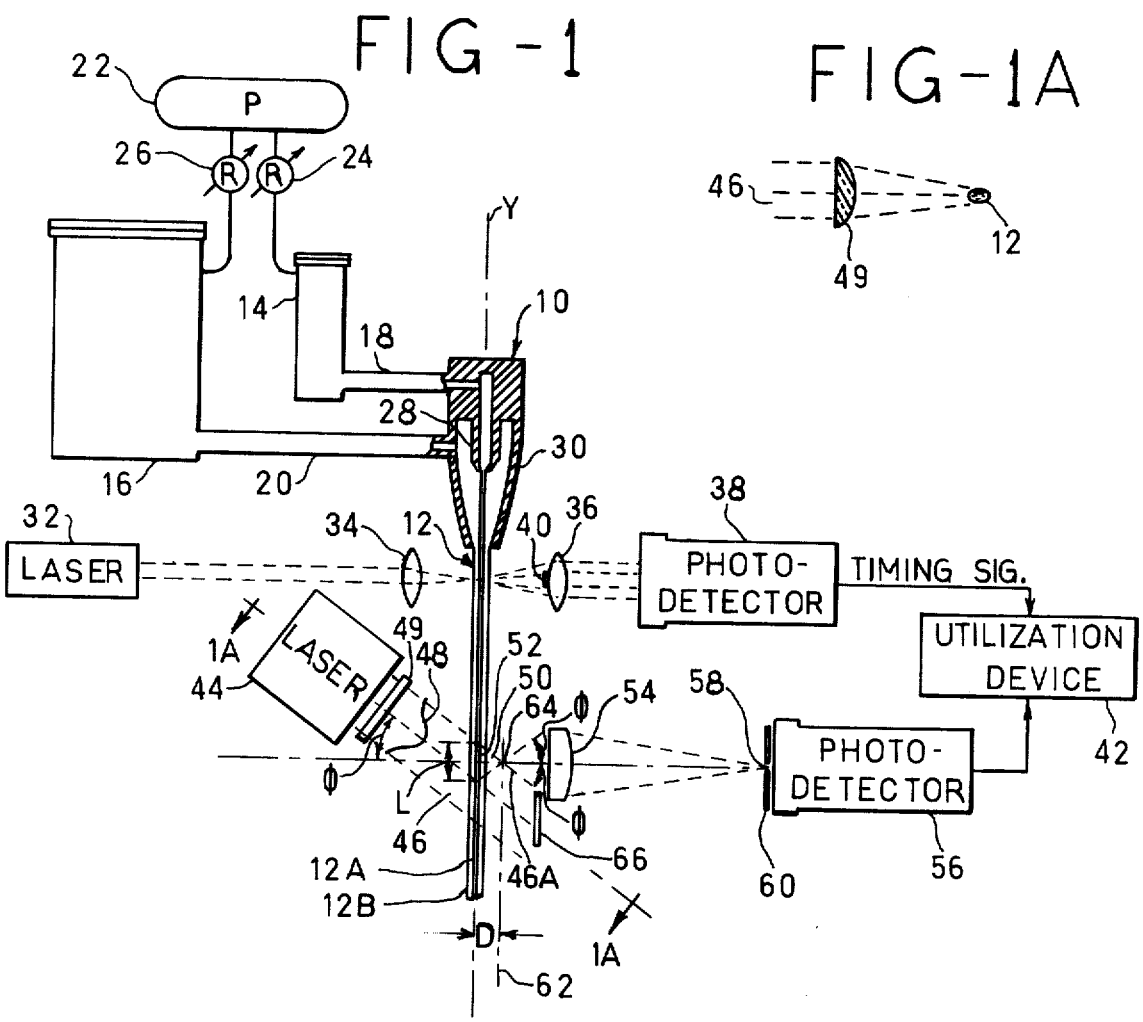
FIG-1
FIG-1A
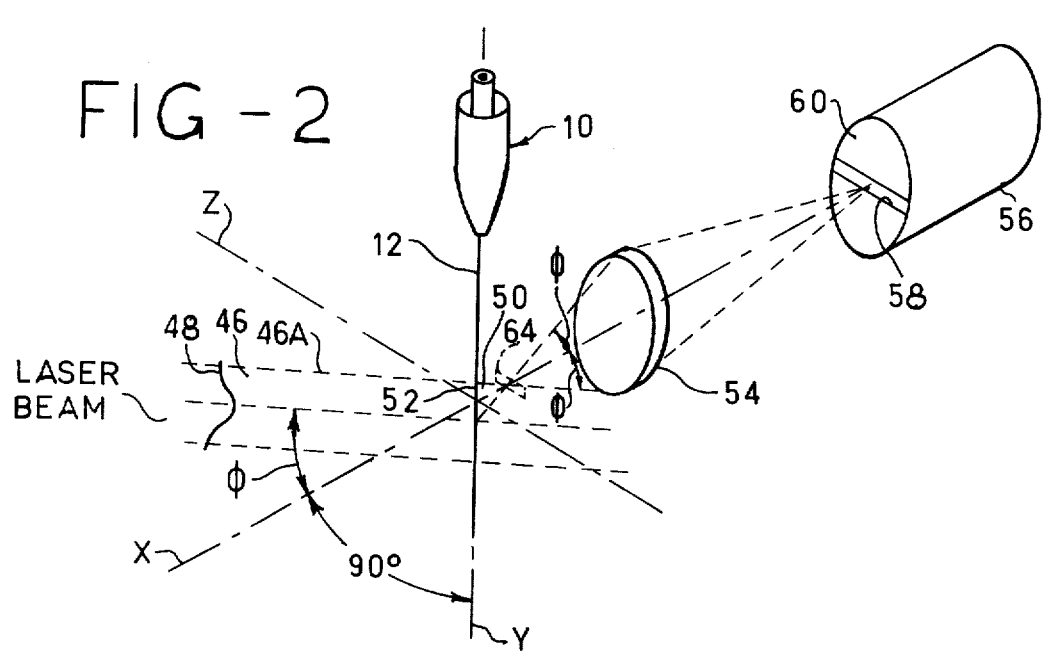
FIG-2

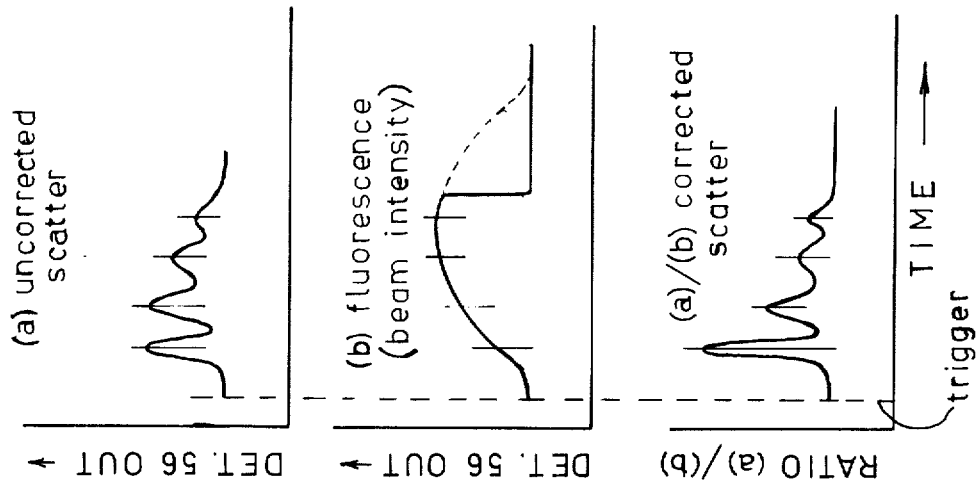
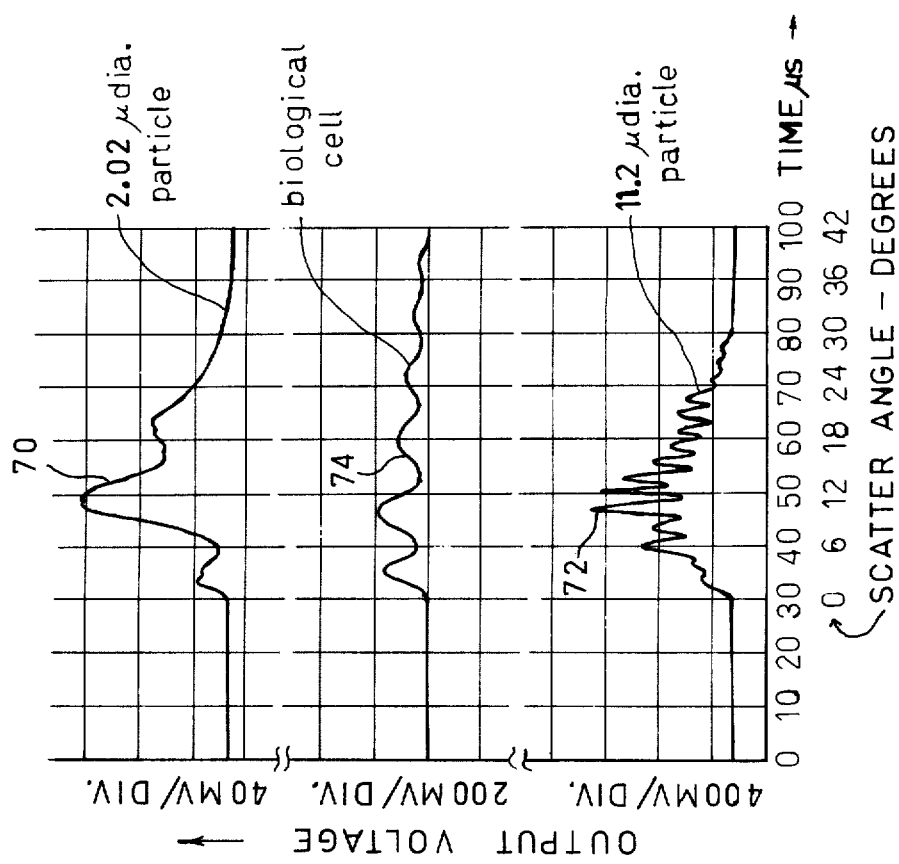

MEASUREMENT OF ANGULAR DEPENDENCE OF SCATTERED LIGHT IN A FLOWING STREAM

The invention described herein was made in the course of work under a grant or award from the Department of Health, Education and Welfare.

BACKGROUND OF THE INVENTION

Photometers for the measurement of the intensity of scattered light at one or more angular positions about a sample cell holding a liquid or particle suspension illuminated by a light beam are known. The sample is confined to the container, or cell, and problems of light absorption, reflection and refraction at the cell wall or various interfaces are encountered. Flow type systems also are known in which the particles are passed across a small illuminated area and scatter light is collected by a number of photodetectors positioned at different angles with respect to the illuminating beam. The signal from each photodetector is used to determine one point in the scatter intensity versus angle characteristic of the particle. A detailed scatter pattern requires many points and thus many individually calibrated detectors and signal processing channels. In alternative arrangements, a single illuminating beam and single photodetector are employed. The particle to be analyzed is stationary, and either the beam or detector acceptance geometry is rotated for measurment through a range of scatter angles. However, such arrangements involve the use of rotating parts which are subject to wear and which are difficult to maintain in proper alignment and operating condition.

It is a general object of this invention to provide an improved particle analyzing method and apparatus which overcome the above-mentioned difficulties and shortcomings of the prior art devices. A more particular object is to provide a particle analyzing method and apparatus for measuring light scattering characteristics of small particles in a flow system which is capable of operating over a wide continuous range of angles, and by means of which the identity of the particle producing the light scattering characteristic may be readily determined.

SUMMARY OF THE INVENTION

The above and other objects and advantages of this invention are achieved by use of a flow system by means of which the particles are contained in a small diameter jet stream for individual passage along a scatter line. Means are provided for directing a beam of generally collimated monochromatic light toward the flow path to illuminate the scatter line. Detector means are provided having a radiation acceptance geometry whose projection intercepts the beam along the scatter line. The detector means includes a photodetector, such as a photomultiplier, and adjacent stop formed with an aperture. Also, an objective is included between the stop and scatter line by means of which an aperture image is located adjacent the scatter line. A real aperture could also be employed, comprising a thin opaque mask with a pinhole or slit therein. The term aperture means is used hereinbelow to identify either a real aperture or an aperture image. The aperture, which may comprise a pinhole or slit, but preferably a slit, and associated objective provides an aperture image having very small dimension (as compared to the length of the scatter line) in the direction of particle travel. Consequently, as the particle traverses the scatter line the angle of scatter light passing through the aperture varies according to the position of the particle along the scatter line. The time varying output from the detector means thereby provides a measure of the light scattering characteristics of the particle.

The output from the detector means may be supplied to any desired utilization device, such as an oscilloscope, correlation circuit, computer, or the like. The system may include particle detecting means upstream from the scatter line for the the production of a timing signal for use in triggering operation of the utilization device. To confine the particle flow to substantially a line a nozzle assembly may be used to provide a coaxial flow stream comprising an inner stream portion of particle containing fluid and an outer stream portion of sheath fluid.

The beam source preferably comprises a laser, and the laser beam may have a gaussian intensity distribution across each axis. Only a section of the varying intensity beam is directed onto the scatter line in a manner such that the particle illumination is less intense for low scatter angles where the scattered light intensity is highest, and is highest for high scatter angles where the scattered light intensity is lowest. As a result of the variation in the illumination intensity, the detector means output voltage versus time curve has a smaller maximum-to-minimum voltage ratio thereby decreasing the dynamic range requirements of the signal processing equipment.

The photodetector output voltage versus time curve obtained by the apparatus depends upon the transfer characteristic of the apparatus. Such transfer characteristic may be determined by using fluorescent particles in the system that emit fluoroescent light uniformly in all directions in proportion to the illumination intensity. A barrier filter is placed in front of the detector to reject scattered light and the resulting detector voltage versus time characteristic is the desired transfer function. Once determined, the apparatus may be arranged for point by point division for corresponding points in time, of the voltage for scattered light by the voltage for fluorescent light to provide an output of the true scattered light intensity versus angle characteristic for the particle producing the scatter signal.

The nature of the present invention will be more fully apparent and understood from a consideration of the following description in light of the drawings wherein like reference characters refer to the same items in the several views.

In the drawings:

FIG. 1 shows in diagrammatic form a particle analyzer of the present invention in one embodiment thereof;

FIG. 1A is a sectional view taken substantially along line 1A—1A of FIG. 1 showing the scatter line illuminating system;

FIG. 2 is a perspective view of a portion of the analyzer shown in FIG. 1;

FIG. 3 shows output waveforms obtainable from the analyzer with different size and type particles;

FIG. 4 shows scatter, fluorescence and corrected scatter waveforms for a typical particle;

Figure 6:
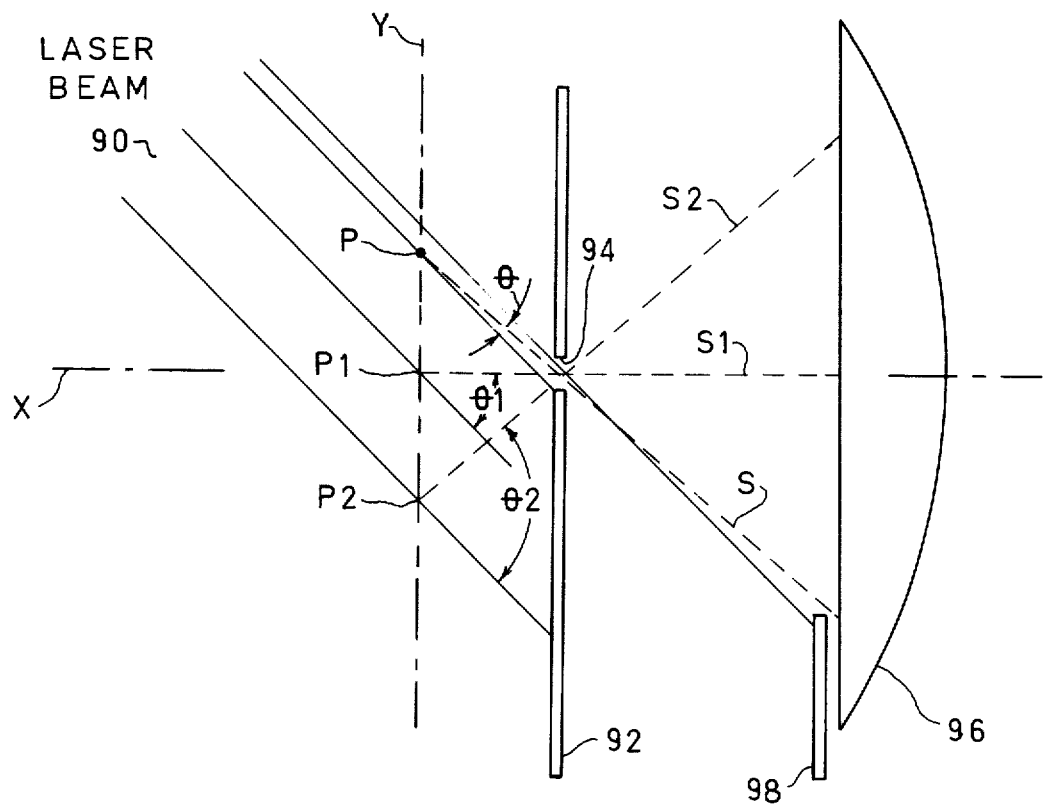
FIG. 6 shows a modified form of particle analyzer embodying this invention.

Reference first is made to FIG. 1 wherein there is shown a nozzle assembly 10 from which liquid containing the particles in suspension is jetted downwardly in a coaxial column or stream generally indicated at 12, along a vertical Y axis. Pressurized reservoirs 14 and 16 are provided, with reservoir 14 containing a supply of the sample liquid in which the particles to be analyzed are suspended, while reservoir 16 contains a supply of particle-free sheath fluid. The reservoirs are connected to the nozzle assembly 10 through conduits 18 and 20 and suitable filter means, not shown, and are pressurized as by means of a gas pressure source 22 connected to the reservoirs through adjustable pressure regulators 24 and 26.

The nozzle assembly 10 includes inner and outer coaxially located nozzles 28 and 30 supplied with fluid from the reservoirs 14 and 16, respectively. The structure is such that the particle containing sample fluid from the nozzle 28 is injected within the nozzle 30 into the center of the flowing steam of sheath fluid. By way of example only, each of the nozzles 28 and 30 may have an outlet diameter of say 50 microns, and may be operated at a pressure of approximately 14 p.s.i. with a small excess sample fluid pressure to produce a jet velocity from the nozzle 30 of 12m/sec. The coaxial flow stream 12, comprising an inner particle-containing portion 12A and an outer, particle-free sheath portion 12B, emerges from the nozzle 30 in the desired coaxial flow condition. Orthogonal X, Y and Z axes are shown for purposes of description, with the stream 12 extending along the vertical Y axis as mentioned above. In flowing through this nozzle the inner stream portion 12A is reduced in diameter to approximately 15 microns within which the particles to be analyzed are confined. With such a coaxial flow configuration, the inner particle-containing portion of the stream is directed along an accurately located well-defined straight line path, at a known velocity, for sensing of particles therein by the novel optical means described below. Also, flow systems of the type illustrated are well known and require no further description.

Particle sensing means for sensing all particles within the jet stream may be included for production of trigger signals for timing purposes. Such particle sensing means are not limited to any particular type of sensor inasmuch as a number of different particle sensing means are known in the prior art. Also, sensing inside of the nozzle 30 or outside thereof may be employed, as desired. For purposes of illustration the particle sensing means are shown located for sensing of particles in the fluid stream directly outside the nozzle. The sensing means may include a light source 32 such as a helium-neon gas laser operating at say 6320A. Illumination from the laser 32 is focused on the inner coaxial portion 12A of the stream by a suitable lens or lens system 34 for highly localized scatter from particles therein. An objective lens or lens system which includes a lens 36 is provided in the beam path of the laser for focusing scatter beams onto the face of a detector 38. A mask 40 which extends over the center of the lens 36 blocks out direct illumination from the laser whereby only laser illumination scattered from illuminated particles in the stream reaches the detector 38. Although different types of well known detectors may be used, preferably a photomultiplier detector is employed because of its large amplification. It will be apparent, then, that an output signal is obtained from the detector 38 for each illuminated particle in the stream. The output from the photodetector 38 is supplied to a utilization unit 42 as a timing signal to trigger operation thereof. It also will be apparent that the amplitude of the signal from the photodetector 38 is directly dependent upon particle size, and use of this relationship may be made in the illustrated arrangement, if desired, in selecting particle sizes to be analyzed.

The novel particle sensing means of this invention, located downstream from the trigger producing sensor, is shown comprising a source 44 of collimated monochromatic radiation. For purposes of illustration a source 44 operating say in the ultraviolet or blue regions may be used which source comprises, for example, an argon laser having a beam 46 which is directed onto the particle-containing central portion 12A of the stream at an angle therewith whereby a cross section of the beam at the stream axis is of elliptical shape. In the illustrated arrangement, the beam has an approximate gaussian intensity distribution across the vertical axis as depicted by the curve 48. The intensity distribution across the horizontal axis is made narrower so as to concentrate the light onto the scatter line. This may be accomplished with cylindrical lens 49, as best seen in FIG. 1A. It here will be understood that the invention is not limited to operation with such a beam distribution but that beams with other energy distributions, such as a generally uniform intensity beam may be employed.

The beam 46 intersects the projected acceptance geometry 50 of the detector section of the optical detection system at the particle-containing stream 12A to define a scattering line 52 (see FIG. 2) along a segment thereof of length L from which light scattered by a particle travelling therealong may be collected. With the illustrated coaxial flow nozzle particles are made to travel along the stream axis as nearly as possible. It will be apparent, however, that particle flow elsewhere within the cross-section of the inner stream is possible, and that the particles cannot, in practice, be confined to travel precisely along the stream axis. The above-identified scattering line 52 comprises, then, a scattering volume but, because the ratio of axial length L to diameter of the volume is large (say 80 to 1) the use of the term scattering line to identify the same is not inappropriate. In any case, the dimension of the sampling volume in the direction of travel of the particle flow is substantially greater than the cross-sectional dimension for operation of the novel analyzer.

Light quanta encountering a particle within the inner coaxial stream are deflected in many directions. Such deflection, or scattering, results from various phenomena, including that of reflection, refraction and diffraction. Light scattered by a particle travelling along the scattering line 52 is collected by an objective 54, comprising a lens or lens system and passed onto the face of a detector 56 through a narrow aperture 58 in a stop 60 adjacent the face of the detector. Although, for purposes of illustration, a simple lens 54 is shown, best results are obtained with a highly corrected multilens system, such as a high quality microscope objective. The Leitz 32X, 0.6NA, 5.7mm working distance, code No. 569002 is an example of a suitable objective. The aperture 58 may be a small diameter hole or slit and preferably, a slit is employed having a horizontal axis in the illustrated X, Z plane along a line parallel with the Z axis. (See FIG. 2) The objective lens axis, coincident with the illustrated X axis, is perpendicular to the particle jet stream axis Y. Preferably, the detector 56 also comprises a photomultiplier having high sensitivity to the relatively faint forward scatter light as a particle passes along the scattering line 52, the photomultiplier output being dependent upon the amplitude of the received scatter light.

The objective 54 images the photodetector aperture 58 at an image plane 62 (FIG. 1) a distance D from the Y axis. In a FIG. 2 the aperture image is shown and identified by the reference numeral 64. The vertical width of the aperture 58 is chosen to produce a very small vertical image width on the order of, say, 13 microns. Where the aperture comprises a slit, as shown, the horizontal dimension of the slit may be sufficient to provide a slit image with a width sufficient to extend beyond the light acceptance cone of the objective 54. With the illustrated arrangement a vertical slit width of 416 microns provides for a 13 micron slit image vertical width.

The objective 54 is positioned at a point along the lens axis X so that the slit image 64 (FIG. 2) is displaced a short distance D (FIG. 1) from the stream axis Y. Alternatively, reference numeral 64 may identify a real aperture comprising a small opening cut into a thin opaque material. In a practical system which has been built and tested a distance D of 730 microns was employed, but it will be apparent that the invention is not limited to any such distance. Vertically, the objective axis X may be located so that the slit image 14 coincides with the upper edge 46A of the illuminating beam 46. (It will be apparent that the beam 46 may be directed upwardly at an angle $\phi$ from the objective axis X instead of downwardly, as shown, in which case the slit image 64 would be located at the lower edge of the beam 46.) In addition the angle $\phi$ between the objective axis X and illuminating beam 46 is chosen so as to equal, or exceed, the arc sine of the numerical aperture of the lens 54 if the system is to work over the widest possible range of angles. The angle between the objective axis X and illuminating beam 46 may be smaller if operation over the widest possible range is not required. In such a case, incident light passing through the aperture 64 must be prevented from entering the detector. In the illustrated arrangement the upper edge 46A of the light beam 46 is directed along the light collection cone of the objective 54 such that the incident light beam 46 avoids the lens. An adjustable mask 66 (FIG. 1) may be included to assure that no incident light enters the lens 54.

Any light reaching the photodetector 56 from the scatter line 52 must pass through the aperture image 64. With the aperture image 64 displaced a distance D of 730 microns from the stream axis Y and with an aperture height of 13 microns (as specified in the above-described example) a vertical collection aperture of 13/730 radians = 1.0° is provided for light collected from any point along the scattering line 52. Where the aperture 58 comprises a slit having a much greater horizontal than vertical dimension the horizontal collection aperture varies according to position along the scattering line 52, and is maximum for rays on the objective optical axis X.

As particles traverse the illuminated scattering line 52, the angle between the illuminating beam 46 and the scattered light passing through the slit image 64 varies from substantially zero to twice the angle $\phi$. Zero angle is excluded because incident light must be prevented from entering the detection system. As noted above, angle $\phi$ is equal to the arc sine of the numerical aperture of the objective lens 54. If, for example only and not by way of limitation, an objective 54 having a numerical aperture of 0.6 is employed, then the angle $\phi$ equals 37° and twice this angle is 74°. However, because of refraction at the jet stream 12 surface the scatter angle range is reduced. For exampple, with a jet stream fluid having a refraction index of, say 1.33, the range of angles is reduced to extend from 0+° to only approximately 56°. It will be seen then that as a particle traverses the scatter line 52 light scatter angles of between 0+° to 56° are sensed, as a function of position of the particle along the scatter line while the scatter light emerging from the jet stream sweeps through an angle of 2 $\phi$ or 74°.

The scanning time is the time required for the particle to travel the length L of the scatter line 52. From the illustrated configuration this distance L is shown to be 2 D · tan (2 $\phi$/2). Substituting the illustrative dimensions there is provided a travel distance of 2(730) · tan (74°/2) = 1100 microns. The scanning time is the time required for the particle to travel this 1100 micron distance, and for a jet stream velocity of 12meters/second the scanning time is 1100microns/12 meters per second = 92 microseconds. Under constant operating conditions the particles passing along the scatter line travel at a substatially uniform velocity. That is, across the inner stream 12A the stream velocity is substantially uniform whereby particles anywhere within the cross section of the inner stream travel with the same velocity along the greater line. The particle velocity is determined by any suitable means. With an angular range of 56° (reduced from 74° because of refraction at the stream surface), the average scanning rate is 56°/92 microseconds = 0.6°/microsecond. As the slit image 64 subtends an angle of 1.0° the angular resolution is 1.0°.

As noted above the aperture 58 is not limited to a slit but may take other forms, such as a pin hole, for example. However, the use of a horizontal slit is preferred to improve the sensitivity of the apparatus by increasing the amount of collected scattered light. Additionally, the use of a slit serves to minimize variations in collected light caused by refraction at the vertical stream surface, which refraction varies in the horizontal plane (but not in the vertical plane) with particle displacement from the jet stream center line Y. Because different elements of the slit are at different angular distances from the illumination axis, and because refraction at the jet stream surface is different in the horizontal and vertical planes, the scattered light versus angle characteristic is modified by a function that varies in a complicated way with vertical collection angle. However, this does not lessen the usefulness of the system since every particle having different light scattering properties will still be characterized by a unique detector 56 voltage output versus time curve.

As is well understood, scattered light intensity varies inversely with scatter angle, i.e. at low scatter angles the light intensity is greatest, and decreases at the scatter angle increases. In accordance with a feature of this invention illumination of the light scatter line 52 varies along the scatter line 52 so that the intensity of incident light is greatest where the measured scatter angle is maximum and is least where the angle is minimum. One way of implementing this feature of the invention is to utilize a portion of the typical laser beam which has a gaussian intensity distribution across each axis, as illustrated by the curve 48 in the drawings. As noted in the drawings, only one half of the beam is used to illuminate the scatter line 52. The beam intensity is minimum for low scatter angles where the scattered light is highest, and increases as the scatter angle increases. Obviously, other means for obtaining a variable intensity beam may be used, For example, a beam having a constant intensity across the beam may be used in conjunction with a variable filter to provide for variable intensity illumination of the particle scattering path. By use of a variable intensity beam the detector 56 output voltage versus time curve will have a smaller maximum-to-minimum voltage ratio and thus the dynamic range requirements of the signal processing equipment will be decreased. Other means for modifying the scattered light versus scatter angle characteristic include the use, at the objective lens 54, or at an equivalent intermediate plane in detection optical system, of a filter having a density that varies vertically across the lens aperture, or a mask that limits the horizontal aperture as a function of vertical angle.

The above described method and apparatus for measuring the light scattering characteristics of small particles may be employed for identifying or classifying particles. To this end, the voltage output from the detector 56 versus time curve as the particle traverses the scatter line 52 is used. For example, the utilization circuit 42 may include an oscilloscope having a cathode ray tube display at the detector 56 output voltage versus time. A triggered oscilloscope may be employed in which the occurrence of an output from the detector 56 initiates the generation of the horizontal sweep, and the detector output is applied as the vertical signal. Alternatively, in the illustrated arrangement, the particle is detected upstream of the scatter line 52, by detector 38 and the output therefrom is used to trigger the horizontal sweep of the oscilloscope. In practice, detection of a particle by the photodetector 38 may be effected immediately outside the nozzle, and the scatter line 52 is located as close to the point of particle detection as is practical to minimize the distance therebetween. With the illustrated coaxial stream flow a substantially constant delay time between observation of a particle by detector 38 and its entering the scatter line 52 is provided. The oscilloscope trace may be recorded, as by photographing the same, for comparison thereof with patterns produced by known particles.

In FIG. 3 curves of detector voltage output versus time produced by different particles are shown. The curves are shown with a common time scale but with different vertical scale divisions. Because the detected light varies in time with the scatter angle, calibration of the horizontal axis in terms of scatter angle, is possible. Any suitable means may be used to measure or determine the particle velocity for proper calibration of the analyzer. In the illustrated arrangement the particle enters the scatter line 52 approximately 30 microseconds after the trigger pulse which occurs at time zero. Trace 70 and 72 identifying 2.02 and 11.2 micron diameter spherical particles, respectively. It will be noted that with the larger diameter microsphere produces a signal approximately 10 times that produced by the smaller diameter microsphere. The light scatter angle spectrum of the larger microsphere includes many more peaks and valleys than that of the smaller microsphere. These, of course, are elements for comparison with patterns made by known particles for identifying an unknown particle.

The invention is particularly useful for analysis of biological cells, and with the illustrated arrangement and specified dimensions analysis of cells having diameters between 5 and 15 microns is possible. Other size ranges may be accommodated by a straight forward change in parameter values, and it will be understood that the invention is not limited to the illustrated and described values. In FIG. 3, trace 74 was obtained from a biological cell. In addition to visual comparison, it will be obvious that electronic signal correlation method and apparatus may be used for detecting and measuring the degree of similarity of the detected signal with one or more reference sinals provided by measurements with known particles. Such correlation techniques are well known and may be accomplished with the use of conventional electronic instruments and computers.

Figure 5:
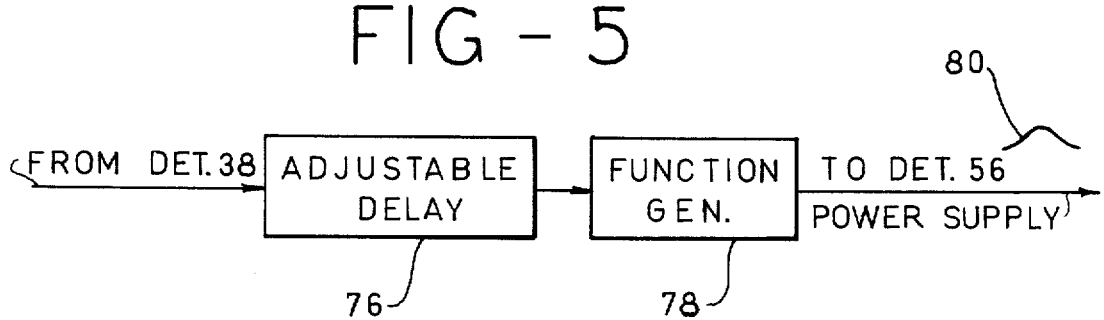
FIG. 5 shows a circuit modification for obtaining corrected scatter waveform output from the apparatus illustrated in FIG. 1.

It will be apparent that the output signal from the detector 56 depends upon the transfer characteristic of the system. An approximate system transfer characteristic may be determined by using fluorescent particles that fluoresce in the presence of the beam 46 from the source 44. A barrier filter is placed in front of the detector 56 to reject scattered light and pass the fluorescent light. The fluorescent particle emits fluorescent light uniformly in all direction in proportion to the illumination intensity, whereby the resulting detector 56 output voltage versus time fraction is the transfer characteristic of the system. Division, point by point for corresponding points in time, of the voltage output for scattered light by the voltage output for the fluorescent light, gives the true scattered light intensity versus scatter angle characteristic for the particle producing the scatter signal. FIG. 4 shows graphs of scatter signal (a), fluorescent signal (b) and corrected scatter signal (a)/(b) for a typical particle. The operation of division of the scattered light voltage by the transfer function of the system may be easily accomplished by any one of a plurality of means. In FIG. 5 there is shown, for example, correcting means which includes an adjustable delay unit 76 which is triggered by the output from the detector 38. The delayed signal from unit 76 is used to trigger operation of a function generator 78 having an output 80 in the shape of the system transfer function. This signal 80 may be applied to any suitable point in the system to control the transfer function. For example, the detector 56 power supply voltage may be varied in accordance therewith to provide the detector itself with the required transfer characteristic.

Operation of the novel method and means for measuring light scattering characteristics of small particles is believed to be apparent from the above description. Briefly, the particles are placed in suspension in a fluid and are passed serially along a jet flow path which includes the light scattering line 52. A generally collimated beam 46 of radiation from the laser 44 is directed onto the jet stream at an angle $\phi$ therewith. Detector means are arranged to collect light scattered by a particle illuminated by the beam 46 as the particle travels along the scatter line 52. The detector means includes an objective lens 54 having an optical axis X which intercepts the jet stream axis Y at right angles thereto. Scatter light passing the lens 54 is directed onto the face of a photodetector 56 through an aperture 58 in a mask 60. Preferably, the aperture comprises a slit having a small dimension in the direction parallel to the stream axis Y. The slit image 64 is located a short distance from the particle flow path adjacent the scatter line 52. In the illustrated arrangement, an edge 46A of the beam 46 emerging from the jet stream extends parallel to and substantially coincides with an edge of the projected acceptance geometry of the detector means. The angle of detectable scattered light from the particle varies in accordance with the position of the particle along the scattering line. The time varying output voltage from the photodetector 56 provides a measure of the scattered light intensity as a function of angle, and is used to identify the particle by comparison with patterns produced by known particles. With the present arrangement the substantially complete scatter angle characteristic for each particle traversing the scatter line is obtained. Not only is the scatter angle information useable for identification of the individual particles by comparison with scatter angle characteristics of known particles, but the information may be used for subsequent separation of particles downstream from the sensing means utilizing any well known separating method, such as that shown in U.S. Pat. No. 3,826,364.

Operation of the apparatus with an actual aperture, rather than aperture image 64 is, of course, possible and such an arrangement is shown in FIG. 6 to which reference now is made. There, a light beam 90 is directed at an angle onto the path of travel of a particle P travelling vertically downwardly along the Y axis. That portion of the line of travel of the particle P along which scatter signals may be received starts approximately at the illustrated position of the particle, and extends downwardly therefrom to a point below the identified point P-2. A stop 92 formed with a small aperture 94 therein is located adjacent the scatter line through which aperture scatter light from the particle P may pass. The scatter light is collected by an objective 96, and directed onto a photodetector, not shown, as in the manner described above with reference to FIGS. 1 and 2. Incident light passing through the aperture 94 is prevented from reaching the light collecting means by use of a light dump or mask 98 shown positioned between the aperture 94 and collector along the path of travel of the incident radiation.

At the illustrated position of the particle P only small scatter angle light reaches the objective. A ray of the scatter light passing the aperture 94, identified by the reference character S, is shown and the small associated scatter angle $\theta$ is identified. Light scattered from the particle P at larger scatter angles is precluded from reaching the objective with the particle at the illustrated position. As the particle travels downwardly along the scatter line increasingly larger scatter angle light passes the aperture 94 for collection. For example, when the particle reaches the point P-1 along the scatter line at the optical axis X of the objective 96, scatter light S-1 reaches the objective. With the particle at this point P-1, scatter light at scatter angle $\theta$-1 is collected, and scatter light at lesser and greater angles is precluded. At point P-2 in the travel of the particle P, scatter light at an angle $\theta$-2 is measured. It will be apparent that although single rays S, S-1 and S-2 are shown in FIG. 6, a small angular range of scatter light passes the aperture 94 for any given position of the particle along the scatter line, as determined by the width of the aperture in the direction of travel of the particle P and the distance of the aperture from the scatter line, which of course, determine the resolution of the system. The remainder of the system may be the same as shown and described above with reference to FIGS. 1–5 and is not repeated here.

The invention having been described in detail in accordance with the requirements of the Patent Statutes, other changes and modifications will suggest themselves to those skilled in the art. For example, illumination of the stream is not limited to use of laser beams. Other illumination sources such as an arc lamp with suitable beam filtering and directing means may be used for illumination at the desired frequency or frequencies. Also, the invention is not limited to detection through the atmosphere as shown. Instead, for example, an immersion system may be employed in which the objective lens, or lens system, 54 is in contact with the sheath fluid 12B of the jet stream. With the illustrated arrangement the range of angles that can be measured is dependent upon the numerical aperture of the objective lens. Objectives for operation in air are available commercially having numerical apertures up to 0.85, which would provide for a collection angle of 116°. But these high numerical aperture lenses are difficult to use because the working distance is small. By placing the objective in contact with the fluid stream, as suggested above, the collection angle of the system may be readily increased. Also, use of the invention is not limited to any particular type particles such as biological cells mentioned above. Other particles, whether solid or liquid, may be investigated by use of this invention. In addition, the incident beam may be directed onto the scattering line at an angle greater than $\phi$ for light scatter measurements over a different range of angles, the low end of the resultant range being substantially equal to the amount by which the increased angle exceeds the angle $\phi$. Also, as mentioned above, the incident beam may be directed onto the scattering line at an angle less than $\phi$ in which case incident light passes through the adjacent aperture, or aperture image, and must be prevented from reaching the photodetector. Also, it will be readily apparent that illumination along the scatter line need not be effected by a generally parallel ray beam as viewed in FIGS. 1, 2 and 6. For example, a focused beam may be used in which converging (or diverging) rays, as viewed in FIGS. 1, 2 and 6, illuminate the scatter line, without focusing at the scatter line. In this case the angle between the incident radiation and objective axis varies along the scatter line and must be known or determined for proper calibration of the system output. It is intended that the above and other such changes and modifications shall fall within the spirit and scope of the invention as defined in the appended claims.

We claim:

1. A particle scattering system employing radiation scattering wherein there is relative movement between the particle and analyzing system comprising,
   means for moving the particle along a scatter line,
   means including a radiation source arranged to project a beam of radiation onto said scatter line,
   detector means having a radiation acceptance geometry whose projection intercepts said beam along the scatter line,
   said projected acceptance geometry including aperture means located adjacent the scatter line and having a dimension in the direction of travel of the particle along the scatter line substantially less than the length of the scatter line such that the angle of scatter radiation detectable by the detector means from said particle varies according to the position of the particle along the scatter line.

2. The particle analyzing system as defined in claim 1 wherein said aperture means comprises a real aperture.

3. The particle analyzing system as defined in claim 1 wherein said aperture means comprises an aperture image.

4. The particle analyzing system as defined in claim 1 wherein said means for moving the particle along a scatter line includes,
a nozzle assembly for producing a stream of particle containing fluid, and
means for jetting the stream from the nozzle assembly along a line which includes said scatter line.

5. The particle analyzing system as defined in claim 4 including second particle detecting means for detecting the particle upstream of said scatter line,
a triggerable utilization unit responsive, when triggered, to the output from said detector means for making a record thereof, and
means for connecting the output from said second particle detecting means to said utilization unit to trigger operation thereof upon detection of the particle upstream of said scatter line.

6. The particle analyzing system as defined in claim 4 wherein the stream from the nozzle assembly comprises a coaxial flow stream having an inner stream portion of particle containing fluid and an outer portion of sheath fluid.

7. The particle analyzing system as defined in claim 6 wherein the coaxial flow stream is jetted into the atmosphere by the nozzle assembly, and the scattering line is located in the atmosphere outside the nozzle along the coaxial flow stream.

8. The particle analyzing system as defined in claim 1 wherein the detector means axis intersects the scatter line axis at substantially right angles, and
the axis of the beam of radiation projected onto the scatter line is located in the plane defined by the intersecting detector means and scatter line axes.

9. The particle analyzing system as defined in claim 1 wherein the intensity of incident beam radiation varies along said scatter line from minimum to maximum as the detectable scatter angle varies from minimum to maximum.

10. The particle analyzing system as defined in claim 9 wherein said radiation source comprises a laser having a beam with a gaussian intensity across the beam cross section, and
wherein substantially one half of which laser beam is projected onto said scatter line.

11. The particle analyzing system as defined in claim 1 wherein said detector means has a voltage output which varies in time with the intensity of scattered light reaching the detector as the particle traverses the scatter line.

12. The particle analyzing system as defined in claim 11 including a utilization unit responsive to the output voltage from the detector means for making a record thereof.

13. The particle analyzing system as defined in claim 1 including,
means for modifying the output from said detector means in accordance with the transfer function of the system to obtain a true scattered light intensity versus angle characteristic output for the particle producing the scatter signal.

14. The particle analyzing system as defined in claim 1 wherein said detector means includes an objective having a numerical aperture the arc sine of which is substantially equal to the angle between the axis of the beam of radiation projected onto the scatter line and the axis of said objective.

15. The particle analyzing system as defined in claim 1 wherein said detector means includes an objective with an optical axis which intersects the scatter line at substantially 90°, and wherein
the axis of the beam projected onto the scatter line intersects the scatter line at an angle substantially equal to the arc sine of the numerical aperture of said objective.

16. The particle analyzing system as defined in claim 15 wherein an edge of said beam projected onto the scatter line extends substantially parallel to and is substantially coincident with an edge of the projected acceptance geometry of said detector means.

17. The particle analyzing system as defined in claim 1 wherein said detector means includes a photodetector and a stop formed with a slit such that the aperture means comprises a slit image having a major dimension extending transversely of the scatter line.

18. A particle analyzing method employing relatively stationary radiation source and detector means for measuring the scatter angle characteristic of a particle travelling along a scatter line at a known velocity relative to said source and detector means comprising,
directing a beam of radiation from a radiation source onto said scatter line to produce scatter radiation from the particle travelling therealong,
collecting for every point of travel of the particle along the scatter line a small angular portion of scatter radiation relative to the total scatter angle measurement and as measured in the direction of particle travel, and
detecting the collected scatter radiation as the particle traverses the scatter line to obtain a time dependent output comprising a measure of the intensity of scatter radiation versus scatter angle characteristic of the particle.

19. The particle analyzing method as defined in claim 18 wherein said collecting step includes positioning, adjacent the scatter line, aperture means having a small dimension in the direction of particle travel as compared to the length of the scatter line for establishing the small angular portion of detectable scatter radiation from the particle at any given particle position along the scatter line.

20. The particle analyzing method as defined in claim 18 including,
producing a coaxial flow stream having an inner stream portion of particle containing fluid and an outer stream portion of sheath fluid,
jetting the coaxial flow stream for travel of the inner stream portion along the scatter line, and
performing the collecting and detecting steps in response to individual particle travel along the scatter line.

21. The particle analyzing method as defined in claim 18 including,
supplying said time dependent output obtained in the detecting step to a triggerable utilization device,
detecting the particle upstream of the scatter line to produce a trigger signal,
supplying said trigger signal to said utilization device to trigger operation thereof while the detected particle traverses the scatter line.

22. The particle analyzing method as defined in claim 18 wherein the beam of radiation directed onto said scatter line has a varying intensity distribution across the beam for minimum particle illumination where the detected scatter angle is minimum and maximum particle illumination where detected scatter angle is maximum.

* * * * *

UNITED STATES PATENT AND TRADEMARK OFFICE
CERTIFICATE OF CORRECTION

PATENT NO. : 3,960,449
DATED : June 1, 1976
INVENTOR(S) : Joseph G. Carleton and Richard G. Sweet It is certified that error appears in the above-identified patent and that said Letters Patent are hereby corrected as shown below:

Title page [73] Assignee should read --The Board of Trustees of Leland Stanford Junior University, Stanford, California-- thereby correcting "Junion" to --Junior-- and Conn." to --California--.

Col. 8, line 10, delete "sinals" and substitute --signals--.

Signed and Sealed this

Twenty-fourth Day of August 1976

[SEAL]

Attest:

RUTH C. MASON
Attesting Officer

C. MARSHALL DANN
Commissioner of Patents and Trademarks